(12) United States Patent
Wu et al.

(10) Patent No.: US 12,403,006 B2
(45) Date of Patent: Sep. 2, 2025

(54) DELIVERY DEVICE

(71) Applicant: SHANGHAI MICROPORT CARDIOFLOW MEDTECH CO., LTD., Shanghai (CN)

(72) Inventors: Xuwen Wu, Shanghai (CN); Baozhu Gui, Shanghai (CN); Jie Mei, Shanghai (CN); Guoming Chen, Shanghai (CN); Yu Li, Shanghai (CN)

(73) Assignee: SHANGHAI MICROPORT CARDIOFLOW MEDTECH CO., LTD., Shanghai (CN)

( * ) Notice: Subject to any disclaimer, the term of this patent is extended or adjusted under 35 U.S.C. 154(b) by 590 days.

(21) Appl. No.: 17/257,139

(22) PCT Filed: Aug. 30, 2019

(86) PCT No.: PCT/CN2019/103838
§ 371 (c)(1),
(2) Date: Dec. 30, 2020

(87) PCT Pub. No.: WO2020/043204
PCT Pub. Date: Mar. 5, 2020

(65) Prior Publication Data
US 2021/0154007 A1 May 27, 2021

(30) Foreign Application Priority Data
Aug. 31, 2018 (CN) .......................... 201811014867.7

(51) Int. Cl.
*A61F 2/24* (2006.01)
*A61F 2/95* (2013.01)
(52) U.S. Cl.
CPC .......... *A61F 2/2427* (2013.01); *A61F 2/2418* (2013.01); *A61F 2002/9505* (2013.01)

(58) Field of Classification Search
CPC ................. A61F 2/2427; A61F 2/2418; A61F 2002/9505
See application file for complete search history.

(56) References Cited

U.S. PATENT DOCUMENTS 5,415,664 A * 5/1995 Pinchuk .................. A61F 2/966
606/198
6,425,916 B1 * 7/2002 Khosravi .................. A61F 2/92
623/1.22
(Continued)

FOREIGN PATENT DOCUMENTS

| CN | 102525698 A | 7/2012 |
| CN | 103446655 A | 12/2013 |

(Continued)

*Primary Examiner* — Alexander J Orkin
(74) *Attorney, Agent, or Firm* — Muncy, Geissler, Olds & Lowe, P.C.

(57) ABSTRACT

A delivery device (1, 1') for loading, delivering and deploying an implant (2) includes a handle (18), an inner tubular core (11), a sheath tube (13) and a guide tip (12). The inner tubular core (11) is coupled, at a proximal end thereof, to an inner tubular core actuation member arranged in the handle (18), and the guide tip (12) is disposed at a distal end of the inner tubular core (11) and fixedly connected to a distal end of the sheath tube (13). The sheath tube is (13) sleeved over the inner tubular core (11). Here, the proximal end of each component refers to the end thereof closer to the handle (18), while the distal end thereof is the end farther away from the handle (18). As the sheath tube (13) is fixedly connected, at the distal end thereof, to the guide tip (12), the implant (2) is loaded at the proximal end of the sheath tube (13) in the delivery device (1, 1'). During deployment of the implant (2), the sheath tube (13) is caused to move toward distal end, that is, the sheath tube (13) continues moving toward a target site for the implant (2), rather than moves backward to the handle (18). This can effectively avoid the problems that (Continued)

may arise from retraction of the sheath tube (13) through a three-dimensionally curved path, such as unstable or even faulty deployment of the implant (2), thus allowing deployment of the implant (2) with enhanced quality.

10 Claims, 2 Drawing Sheets

(56) References Cited

U.S. PATENT DOCUMENTS

| | | | | |
|---|---|---|---|---|
| 6,582,460 | B1* | 6/2003 | Cryer | A61F 2/95 623/1.11 |
| 2006/0020334 | A1* | 1/2006 | Lashinski | A61F 2/2418 623/2.11 |
| 2006/0135961 | A1* | 6/2006 | Rosenman | A61B 17/0057 604/95.04 |
| 2008/0147182 | A1* | 6/2008 | Righini | A61F 2/243 623/2.11 |
| 2008/0255661 | A1* | 10/2008 | Straubinger | A61F 2/2427 623/2.36 |
| 2009/0069890 | A1* | 3/2009 | Suri | A61F 2/2433 623/2.11 |
| 2010/0082089 | A1* | 4/2010 | Quadri | A61F 2/2418 623/1.11 |
| 2010/0100167 | A1* | 4/2010 | Bortlein | A61F 2/95 623/1.11 |
| 2010/0286768 | A1* | 11/2010 | Alkhatib | A61F 2/2439 623/2.11 |
| 2011/0082464 | A1* | 4/2011 | Douk | A61F 2/95 606/108 |
| 2011/0202128 | A1* | 8/2011 | Duffy | A61F 2/2436 623/2.11 |
| 2011/0295354 | A1* | 12/2011 | Bueche | A61F 2/966 623/1.11 |
| 2011/0307049 | A1* | 12/2011 | Kao | A61F 2/966 623/1.11 |
| 2013/0116772 | A1* | 5/2013 | Robinson | A61F 2/966 623/1.12 |
| 2013/0166020 | A1* | 6/2013 | Hillukka | A61F 2/9525 623/2.11 |
| 2013/0231735 | A1* | 9/2013 | Deem | A61F 2/2436 623/2.11 |
| 2013/0274870 | A1* | 10/2013 | Lombardi | A61F 2/2427 623/2.11 |
| 2014/0005768 | A1* | 1/2014 | Thomas | A61M 25/0136 623/2.11 |
| 2014/0052238 | A1* | 2/2014 | Wang | A61F 2/2436 623/2.11 |
| 2014/0107757 | A1 | 4/2014 | Dorn et al. | |
| 2015/0127092 | A1* | 5/2015 | Straubinger | A61F 2/2436 623/2.11 |
| 2015/0272731 | A1* | 10/2015 | Racchini | A61F 2/2436 623/2.11 |
| 2016/0158497 | A1* | 6/2016 | Tran | A61F 2/2436 604/95.04 |
| 2017/0165064 | A1 | 6/2017 | Nyuli et al. | |
| 2017/0325953 | A1* | 11/2017 | Klima | A61F 2/2436 |
| 2018/0049873 | A1 | 2/2018 | Manash et al. | |
| 2018/0117304 | A1* | 5/2018 | Koop | A61N 1/372 |

FOREIGN PATENT DOCUMENTS

| | | |
|---|---|---|
| CN | 107496055 A | 12/2017 |
| CN | 108245290 A | 7/2018 |
| CN | 108245293 A | 7/2018 |
| EP | 3345574 A1 | 7/2018 |
| JP | 2009511229 A | 3/2009 |
| JP | 2009195712 A | 9/2009 |
| KR | 10-2012-0124498 | 11/2012 |

* cited by examiner

DELIVERY DEVICE

TECHNICAL FIELD

The present invention relates to the technical field of medical instruments and, in particular, to a delivery device.

BACKGROUND

Accurate and reliable positioning of a stented prosthetic mitral valve is crucial for the success of a transcatheter mitral valve repair (TMVR) operation. The mitral valve is structurally more complicated than the aortic valve due to high shape irregularity of the annulus, multiple chordae tendineae in the ventricles of the heart that may seriously interfere with the implantation and positioning of the prosthetic valve, as well as very high intracavitary pressures generated by ventricular contraction. Therefore, an improper design of a positioning device may become a direct cause of a series of fatal complications.

A device for delivering a stented prosthetic mitral valve typically includes a sheath tube, which will experience significant radial forces from the stent and thus has to be made from a stiff material in order to avoid damage from the stent. Such a stiff sheath tube is typically long (50-70 mm), making it only bendable (during the passage of a guide wire therethrough or in the course of deployment) at a very large radius of curvature, which is much greater than space shape of anatomical geometries. Moreover, during implantation of the stented prosthetic mitral valve, once the system has been deployed in place through bending control by a delivery catheter, no change is allowed in the delivery path throughout the deployment process, in order to avoid any adverse influence on the positional accuracy of the deployed valve. To sum up, because the sheath tube of the delivery device is stiff and long, and since the delivery catheter that provides the bending control must be able to maintain a fixed geometrical configuration, the delivery catheter that has effectuated the bending control has to also exhibit high stiffness. As a result, it will be difficult to retract the stiff sheath tube (which is a straight tube) through the curved path (which conforms to a radius of the anatomical geometry of the target site), and forcible retraction may affect the bending control of the delivery catheter and is detrimental to stable deployment of the prosthetic valve. Furthermore, in the deployment process, it is very likely for the catheter to move forward or backward and thus displace the prosthetic mitral valve that has been partially deployed. This can become a cause for degraded deployment quality of the valve prosthesis.

In addition, in order to adapt to the shape of the mitral annulus and better conform to its anatomy, the stent is usually designed with an inflow portion and an outflow portion having a radius that is greater than a radius of the inflow portion. The inflow portion is configured to be anchored above the native annulus (i.e., an intra-atrial end), and the outflow portion below the native annulus (i.e., an intra-ventricular end). Such a design can facilitate the anchoring of the valve stent. Conventionally, the delivery of the valve prosthesis would involve retrieval and self-expansion of the sheath tube, with the outflow portion of the stent being released prior to the release of the inflow portion. However, in practice, accurate positioning of the inflow portion against the annulus is difficult and often with positional deviations, which cannot be eliminated by adjustments even when identified.

Therefore, there is an urgent need for a delivery device, which is capable of avoiding the sheath tube from passing through a three-dimensionally curved path during the deployment of the stent while ensuring that the valve stent has a high coaxiality with the annulus and is stable during deployment, i.e., ensuring a high valve repair quality.

SUMMARY OF THE INVENTION

It is an object of the present invention to provide a delivery device, which can ensure stable deployment of an implant with high coaxiality while avoiding introducing a sheath tube for the deployment through a three-dimensionally curved path.

To this end, the provided delivery device is configured to load, deliver and deploy an implant and comprises a handle, an inner tubular core, a sheath tube and a guide tip. The inner tubular core is coupled, at a proximal end thereof, to an inner tubular core actuation member arranged in the handle. The guide tip is disposed at a distal end of the inner tubular core and fixedly connected to a distal end of the sheath tube, and the sheath tube is sleeved over the inner tubular core.

Optionally, the delivery device may further comprise:
an inner tube disposed between the inner tubular core and the sheath tube, the inner tube being fixed, at a proximal end thereof, to an inner tube fastener arranged in the handle; and
an anchor, wherein the anchor is in fixed connection with the inner tube and is configured to retain the implant.

Optionally, the guide tip may have conical shape, wherein the distal end of the sheath tube is in smooth and fixed connection with a proximal end of the guide tip.

Optionally, the delivery device may further comprise a transition member, wherein: the transition member is configured as a tubular structure sleeved over the inner tube; the transition member is so disposed within the sheath tube; and the transition member and the sheath tube are partially fitted against each other.

Optionally, the sheath tube may be smoothly and detachably coupled, at a proximal end thereof, to the transition member by means of static friction.

Optionally, the transition member may comprise a transition section and a catheter section in communication with each other, the transition section being configured as a hollow protrusion, the transition section being smoothly and detachably coupled, at a distal end thereof, to the proximal end of the sheath tube, the transition section having a proximal end in smooth and fixed connection with a distal end of the catheter section, the catheter section being coupled, at a proximal end thereof, to a catheter actuation member arranged in the handle.

Optionally, the delivery device may further comprise a bending controllable tube sleeved over the catheter section, the bending controllable tube abutting, at a distal end thereof, against the transition section, the bending controllable tube being coupled, at a proximal end thereof, to a bending controllable tube actuation member arranged in the handle, wherein the bending controllable tube comprises a bending control mechanism adapted to adjust an angle of deflection from an axial direction of the bending controllable tube.

Optionally, the transition member may comprise a transition section, wherein the transition section is configured as a hollow protrusion, and the transition section is smoothly and detachably coupled, at a distal end thereof, to the proximal end of the sheath tube.

Optionally, the delivery device may further comprise a bending controllable tube sleeved over the inner tube, wherein: the bending controllable tube is fixed, at a distal end thereof, to a proximal end of the transition section; the bending controllable tube is coupled, at a proximal end thereof, to a bending controllable tube actuation member arranged in the handle; and the bending controllable tube comprises a bending control mechanism adapted to adjust an angle of deflection from an axial direction of the bending controllable tube.

Optionally, the protrusion may comprise: a half-cone structure, a hemisphere structure or a circular frustum structure.

Optionally, at least a portion of the transition section may have a gradually decreased outer diameter in a direction from the distal end to the proximal end of the transition section.

Optionally, the anchor may have a plurality of grooves provided thereon.

In the provided delivery device, the distal end of the sheath tube is fixed to the guide tip, and the implant is loaded into the delivery device by the proximal end of the sheath tube. During deployment of the implant, the sheath tube is caused to move toward distal end, that is, the sheath tube continues moving to the target site of the implant, rather than moves backward to the handle. This can effectively circumvent the problems that may arise from retraction of the sheath tube through a three-dimensionally curved path, such as unstable or even faulty deployment of the implant. Moreover, in view of the fact that the implant is structured as having a radius greater in the inflow portion than in the outflow portion, it is designed that the inflow portion of the implant is released prior to the release of the outflow portion of the implant. Once the inflow portion of the implant is released, a check against the target site may be performed, and the implant can be adjusted in a timely manner as soon as it is found that inaccurate positioning would take place. This enables more accurate deployment of the implant with enhanced quality.

In these figures, 1 and 1': an implant delivery device; 11, an inner tubular core; 12, a guide tip; 13, a sheath tube; 14, an inner tube; 15, an anchor; 151, a smaller-diameter member; 16, a transition member; 161, a transition section; 162, a catheter section; 17, a bending controllable tube; 18, a handle; 2, an implant; 21, an attachment lug; 22, an outflow portion; and 23, an inflow portion.

DETAILED DESCRIPTION

Specific embodiments of the present invention will be described in greater detail below with reference to the accompanying drawings. Features and advantages of the invention will be more readily apparent from the following detailed description, and from the appended claims. Note that the figures are provided in a very simplified form not necessarily presented to scale, with the only intention of facilitating convenience and clarity in explaining the disclosed embodiments.

As used herein, the term "smooth connection" (detachable or not) refers to a connection of two components with a smooth continuation at their outer surfaces, which imparts high reliability to the whole structure (in particular of a catheter assembly) without causing damage to human tissues during use.

As mentioned in the Background section, during the deployment of an implant, a sheath tube (which is a straight tube) used in conventional delivery devices is stiff and thus difficult to be retracted through a curved path, and forcible retraction may affect the bending control provided by a bending controllable tube and is detrimental to stable deployment of the prosthetic valve. Moreover, in the deployment process, it is very likely for the catheter to move forward or backward and thus displace the prosthetic mitral valve that has been partially deployed. This can become a cause for degraded deployment quality of the valve prosthesis. Further, when using a deployment method involving retrieval of the sheath tube and self-expansion of the implant, an outflow portion of the implant will be released prior to the release of an inflow portion of the implant. However, in practice, accurate positioning of the inflow portion against a target site is difficult and is often with positional deviations, which cannot be eliminated by adjustments even when identified.

Figure 1:
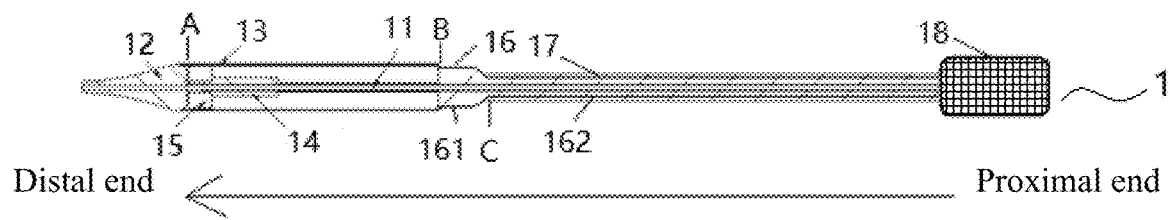
FIG. 1 is a schematic illustration of the structure of an implant delivery device according to a first embodiment of the present invention.
Figure 5:
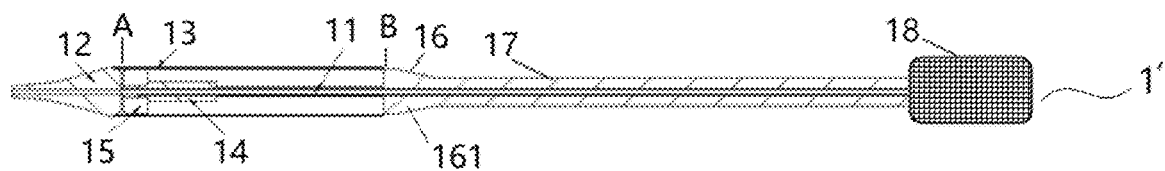
FIG. 5 is a schematic illustration of the structure of an implant delivery device according to a second embodiment of the present invention.

In view of the above, as shown in FIG. 1 or 5, the present invention proposes a delivery device 1 for loading, delivering and deploying an implant. The delivery device 1 is composed of a catheter assembly and a handle 18. Specifically, the catheter assembly includes an inner tubular core 11, a guide tip 12, a sheath tube 13, an inner tube 14, an anchor 15, a transition member 16 and a bending controllable tube 17.

In addition, for convenience of description, as shown in FIG. 1, it is defined herein that any end facing toward the catheter assembly is a distal end and that facing toward the handle 18 is a proximal end. In other words, any end located farther away from the handle 18 is defined as a distal end and that closer to the handle 18 as a proximal end.

Figure 2:
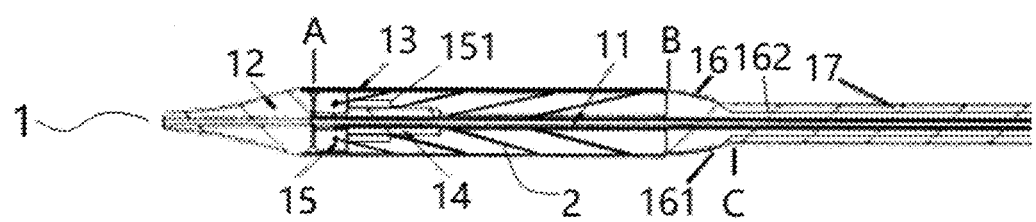
FIGS. 2 to 4 schematically illustrate loading and deploy operation of the implant delivery device according to the first embodiment of the present invention.

As shown in FIGS. 1 to 2, a proximal end of the inner tubular core 11 is coupled to an inner tubular core actuation member arranged in the handle 18 so that the handle 18 is able to cause axial movement of the inner tubular core 11, and the inner tubular core 11 is fixed, at a distal end thereof, to the guide tip 12. The sheath tube 13 has a distal end in smooth and fixed connection with a proximal end of the guide tip 12. That is, the outer surfaces at the connection where the distal end of sheath tube 13 connects with the proximal end of the guide tip 12 are continuous and smooth. The sheath tube 13 is sleeved over the inner tubular core 11.

The anchor 15 is fixed to the inner tube 14, and the inner tube 14 is disposed between the inner tubular core 11 and the sheath tube 13. The inner tube 14 is fixed, at a proximal end thereof, to an inner tube fastener in the handle 18. In this way, the inner tube 14 is limited by the handle 18 at six degrees of freedom (i.e., three translational degrees of freedom along the three orthogonal coordinate axes X, Y and Z and three rotational degrees of freedom about these three axes).

The transition member 16 is a tubular structure sleeved over the inner tube 14 and preferably has a distal end that is nested within the sheath tube 13 in such a manner that the two components are partially fitted and thus sealed against each other. In some embodiments, the distal end of the transition member 16 (i.e., the part of the transition member 16 nested within the sheath tube 13) has a maximum outer diameter that is slightly smaller than an inner diameter of the sheath tube 13, ensuring that the transition member 16 is snugly received in the sheath tube 13 without any clearance therebetween. This means that the two components are fitted against each other where the maximum outer diameter of the distal end of the transition member 16 is defined (i.e., the part of the transition member 16 received within the sheath tube 13 is fitted against the sheath tube 13). A proximal end of the sheath tube 13 is smoothly and detachably coupled to the transition member 16. That is, the outer surfaces at the connection where the proximal end of the sheath tube 13 connects with the transition member 16 are smooth and continuous. In other embodiments hereof, the maximum outer diameter of the transition member 16 at the distal end thereof may also be equal to the inner diameter of the sheath tube 13. In these cases, the transition member 16 can also be nested in the sheath tube 13, so that they are fitted against each other where the maximum outer diameter of the distal end of the transition member 16 is defined, thereby achieving a detachably coupling between the transition member 16 and the sheath tube 13. In yet other embodiments hereof, the maximum outer diameter of the transition member 16 at the distal end thereof may also be slightly greater than the inner diameter of the sheath tube 13. In these cases, the two components can also be connected together by an interference fit, thereby achieving a fitting at the maximum outer diameter of the distal end of the transition member 16, thus a seal therebetween can be improved. More preferably, the sheath tube 13 and transition member 16 are sealed against each other, and the proximal end of the sheath tube 13 is smoothly and detachably coupled to the transition member 16. The bending controllable tube 17 is adapted primarily to adjust an angle of deflection of the catheter assembly from an axial direction thereof. The transition member 16 may comprise at least two configurations, and the present invention illustrates two embodiments according to different configurations of the transition member 16.

Embodiment 1

As shown in FIG. 1, a delivery device 1 according to this embodiment is composed of a catheter assembly and a handle 18. Specifically, the catheter assembly includes an inner tubular core 11, a guide tip 12, a sheath tube 13, an inner tube 14, an anchor 15, a transition member 16 and a bending controllable tube 17.

A proximal end of the inner tubular core 11 is coupled to an inner tubular core actuation member arranged in the handle 18 so that the handle 18 is able to cause axial movement of the inner tubular core 11, and the inner tubular core 11 is fixed at a distal end thereof to the guide tip 12. The sheath tube 13 has a distal end in a smooth and fixed connection with a proximal end of the guide tip 12 at position A. The sheath tube 13 is sleeved over the inner tubular core 11. In this way, the inner tubular core 11 can be driven to cause axial movement of each of the guide tip 12 and sheath tube 13.

Optionally, the guide tip 12 is streamlined in design and is preferably made of a polymer. The sheath tube 13 is configured to press and retain an implant 2. The inner tubular core 11 causes forth-and-back movement of the whole of the guide tip 12 and sheath 13, thereby achieving the loading and deployment of the implant 2. The sheath tube 13 may be formed of a metal, a polymer/metal composite material or the like. The inner tubular core 11 may be fabricated from a polymer, a polymer/metal composite material, a metal or the like.

Optionally, as shown in FIG. 1, the guide tip 12 comprises a shape of conical, with the distal end of the sheath tube 13 being in a smooth and fixed connection with the proximal end (the end with a greater diameter) of the guide tip 12. Such a structural design enables reduced resistance to movement of the sheath tube 13 in the direction from the proximal to the distal end and enhanced stability in the implantation process. Of course, the guide tip 12 may comprise an alternative shape, such as a circular frustum or a hemisphere, and has at least one portion that is gradually decreased in outer diameter along the proximal to the distal end of the guide tip 12.

According to the present invention, the handle 18 is not limited to any particular type and may be implemented as any one of a hand-driven handle, a power-driven handle or a hybrid hand- and power-driven handle.

As shown in FIG. 1, the sheath tube 13 has a proximal end in smooth and detachable connection with the transition member 16 at position B. The transition member 16 is a tubular structure sleeved over the inner tube 14. In this embodiment, the transition member 16 includes a transition section 161 and a catheter section 162, which communicate with each other and may be fabricated either separately from, or integrally with, each other. The transition member 16 may be fabricated from a polymer, a polymer/metal composite material, a metal or the like.

The transition section 161 has a distal end, which is smoothly and detachably coupled (e.g., by static friction) to the proximal end of the sheath tube 13 at the position B, and a proximal end in smooth and fixed connection with a distal end of the catheter section 162. The transition section 161 has at least one section gradually decreased in outer diameter along the direction from the distal to proximal end of the transition section 161. For example, the transition section 161 may be a hollow protrusion in the shape of a half cone, a hemisphere, a circular frustum or the like, which has a maximum outer diameter slightly smaller than an inner diameter of the sheath tube 13. The sheath tube 13 may receive and wrap part of the transition section 161, thus providing a smooth transition at the proximal end of the sheath tube 13 to a connecting portion of the bending controllable tube 17, as described below. The catheter section 162 is a tubular structure sleeved over the inner tube 14 and has a proximal end coupled to a catheter actuation member arranged in the handle 18, so that the handle 18 is able to cause axial movement of the catheter section 162. In this way, the moving catheter section 162 can drive the transition section 161 to move axially therewith.

The delivery device further comprises a bending controllable tube 17. The bending controllable tube 17 is sleeved over the catheter section 162 and has an inner diameter greater than an outer diameter of the catheter section 162. In this way, the catheter section 162 is axially moveable within the bending controllable tube 17. The bending controllable tube 17 abuts, at a distal end thereof, against the transition section 161. That is, as shown in FIG. 1, a proximal end of the transition member 16 is brought into contact with, but is not fixedly connected to the bending controllable tube 17 at position C. The bending controllable tube 17 is coupled, at a proximal end thereof, to a bending controllable tube actuation member arranged in the handle 18, so that the handle 18 is able to cause axial movement of the bending controllable tube 17.

The bending controllable tube 17 includes a bending control mechanism for adjusting an angle of deflection of the bending controllable tube 17 from an axial direction and hence of the entire catheter assembly from an axial direction.

The bending controllable tube 17 may be a reinforced polymer tube, a reinforced metal tube or a tube consisting of modular metal sections, etc., with bending control capabilities. Specifically, the reinforced polymer tube may be a polymer tube embedded therein with one, two or more metal wires. By pulling the metal wires, bending control may be achieved and further by pulling different metal wires, bending control of different directions may be achieved. The reinforced metal tube may be a metal tube fabricated by braiding or cutting. The braiding may be spiral braiding or cross braiding, while the cutting may be accomplished by a laser to form cutouts. The metal tube fabricated by braiding or cutting may be embedded therein with one, two or more metal wires. By pulling the metal wires, bending control may be achieved and further by pulling different metal wires, bending control of different directions may be achieved. Further, a tube with modular metal sections is a tube consisting of multiple solid or hollow modular sections that are connected together in series. Such an active bending control design can facilitate to pass through more complicated bending contours in order to reach a target site.

As shown in FIG. 1, the anchor 15 is fixed to the inner tube 14 and is configured to secure the implant 2. The inner tube 14 is disposed between the inner tubular core 11 and the sheath tube 13 and has a proximal end in fixed connection with an inner tube fastener arranged in the handle 18. In this way, the inner tube 14 is limited by the handle 18 at six degrees of freedom (i.e., three translational degrees of freedom along the axes X, Y and Z and three rotational degrees of freedom about axes X, Y and Z), in order to better support the implant 2. The inner tube 14 may be formed of a polymer, a polymer/metal composite material, a metal or the like.

Optionally, the anchor 15 may be provided thereon with a plurality of grooves (not shown) for securing the implant 2. The anchor 15 may be formed of a metal or polymer. Preferably, as shown in FIGS. 3 to 5, the anchor 15 is connected, at a proximal end thereof, to a smaller-diameter member 151 made of a metal or polymer, which is also secured to the inner tube 14 to better support the implant 2 by preventing the implant 2 from twisting during loading and retrieval.

As shown in FIG. 1, the inner diameter of: the inner tubular core 11, the inner tube 14, the catheter section 162, the bending controllable tube 17 and the sheath tube 13 increase sequentially. Preferably, the inner tubular core 11, the inner tube 14, the catheter section 162, the bending controllable tube 17 and the sheath tube 13 are arranged coaxially.

Figure 3:
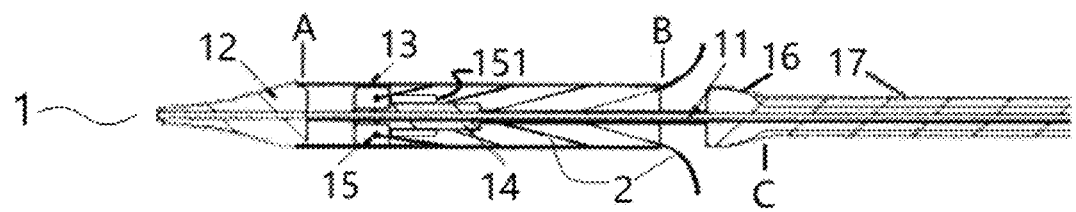
Figure 4:
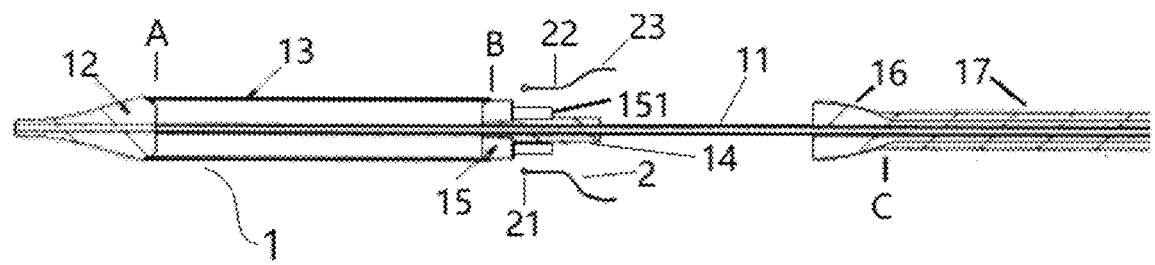

Referring to FIGS. 2 to 4, a method for implanting an implant using the delivery device 1 as defined above according to an embodiment of the present invention may include the steps of:

S1: providing the implant delivery device 1 and the implant 2 to be loaded;

S2: causing the sheath tube 13 to move toward distal end until exposing the anchor 15 by driving the inner tubular core 11 through manipulating the handle 18; attaching one end of the implant 2 to the anchor 15; and causing the sheath tube 13 to move toward proximal end by driving the inner tubular core 11 through manipulating the handle 18, so that the implant 2 is crimped and then is loaded into the sheath tube 13;

S3: driving the entire catheter assembly by an external force, thus causing the sheath tube 13 and the anchor 15 to move toward distal end in synchronization therewith; and S4: upon the implant 2 being delivered to the target site, deploying the implant 2 by causing the sheath tube 13 to move toward distal end through driving the inner tubular core 11 by manipulating the handle 18.

This process may involve loading, delivery and deployment. By driving a bearing through manipulating the handle 18 in a power- or hand-driven manner, causing the inner tubular core actuation member to move forward and backward (i.e., the inner tubular core 11 moves under the action of the inner tubular core actuation member). Further, driven by the inner tubular core 11, the sheath tube 13 and the guide tip 12 move axially with respect to the inner tube 14, thus achieving operations such as loading and deployment of the implant 2. A more detailed description of this process is set forth below.

First of all, step S1 is carried out, in which the implant delivery device 1 and the implant 2 to be loaded are provided. In this embodiment, the implant 2 may be implemented as a prosthetic mitral valve stent, which, as shown in FIG. 4, includes two attachment lugs 21, an outflow portion 22 and an inflow portion 23, which are sequentially connected in this order, with the inflow portion 23 having a radius that is greater than a radius of the outflow portion 22. It will be appreciated that the prosthetic mitral valve stent is merely an example of the implant 2, and does not imply any limitation upon the implant 2. Although geometric of a common prosthetic mitral valve stent are exemplified in this embodiment, the present invention is not limited to any particular geometric of any valve stent.

Subsequently, step S2 is performed, in which loading of the implant 2 is accomplished by driving the inner tubular core 11, through manipulating the handle 18, to cause the guide tip 12 and sheath tube 13 to move toward the distal end as a whole, until the grooves on the anchor 15 are exposed, as shown in FIG. 4. The attachment lugs 21 of the implant 2 are then snapped in the respective grooves so as to serve to facilitate stability of the stent during loading. The handle 18 is manipulated so that the inner tubular core 11 is driven to move toward the proximal end, thus crimping the outflow portion 22 of the implant 2, as shown in FIG. 3. With continued movement of the sheath tube 13, the inflow portion 23 of the implant 2 is also crimped. In this way, the entire implant 2 is wrapped by the sheath tube 13, with its distal end abutting against an end face of the guide tip 12. At this point, loading of the implant 2 is achieved, as shown in FIG. 2

Afterwards, step S3 is performed in which delivery of the implant 2 is accomplished by exerting an external force to introduce the catheter assembly in the delivery device 1 over a guide wire into the body of a patient via a puncture. The catheter assembly is then advanced as a whole through the femoral vein and across the interatrial septum. In this way, the sheath tube 13 and the anchor 15 are delivered in synchronization to distal end, until to the target site (i.e., the site of the lesion).

Finally, step S4 is performed in which deployment of the implant 2 is accomplished by adjusting an angle of deflection of the sheath tube 13 (the adjustment is achieved by tuning the bending controllable tube 17 and is followed by fixing the bending controllable tube 17 in place) after it has reached the target site, which results in coaxiality with the native mitral annulus. A "Forward" button on the handle 18 is then pressed, causing the guide tip 12 and the sheath tube 13 to move toward distal end, which results in beginning of deployment of the implant 2. This is continued until the implant 2 is completely deployed to the target site and detached from the catheter assembly, as shown in FIGS. 2 to 4.

Specifically, during movement of the sheath 13 toward the distal end, the inflow portion 23 of the implant 2 is first released, followed by the release of the outflow portion 22 of the implant 2 under the effect of further movement of the sheath tube 13, until the proximal end of the sheath tube 13 reaches the anchor 15 and the grooves on the anchor 15 are exposed. At this point, complete deployment of the implant 2 is achieved.

In addition, after the completion of the implantation of the implant 2, it is necessary to retrieve the catheter assembly in the implant delivery device 1. The retrieval can be accomplished by causing the catheter section 162 of the transition member 16 and hence the transition section 161 thereof to move toward the distal end so that the transition section 161 of the transition member 16 reaches a position in relation to the sheath tube 13 as shown in FIG. 1, where they are coupled together smoothly and detachably. The handle 18 is then manipulated to retrieve the catheter assembly from the patient's body.

In the implant delivery device 1 according to this embodiment of the present invention, the sheath tube 13 is fixed to the guide tip 12, and the inner tubular core 11 is provided. In the loading process, the inner tubular core 11 drives both the sheath tube 13 and the guide tip 12 to move toward distal end until the anchor 15 is exposed. After the attachment lugs 21 of the implant 2 are attached to the anchor 15, the inner tubular core 11 is controlled to drive the sheath tube 13 and the guide tip 12 to move toward proximal end to crimp the implant 2, until accomplishing the loading of the implant 2. In the deployment process, the inner tubular core 11 causes the sheath tube 13 and the guide tip 12 to move toward distal end, which allows release of the implant's inflow portion 23 and then of its outflow portion 22. In this way, it is unnecessary to retract the sheath tube 13 during deployment of the implant 2, dispensing with its need to travel through a three-dimensionally curved path. This can effectively avoid the problems that may arise from retraction of the sheath tube 13 through a three-dimensionally curved path, such as unstable or faulty deployment of the implant 2. In practice, since the implant 2 is structured as having a radius greater in the inflow portion than in the outflow portion, when the outflow portion 22 is released, it will interfere with leaflets of the implant 2. As a result, it will be different to remedy any found unsatisfactory positioning of the implant by adjustment. In contrast, according to the present invention, since the sheath tube 13 employs a distal end deployment design, the inflow portion 23 of the implant 2 will be released prior to the release of the outflow portion 22. In this way, once the inflow portion 23 is released, a check against the target site is allowed, and the implant can be adjusted in a timely manner as soon as it is found that inaccurate positioning would take place. Therefore, the delivery device according to the present invention enables accurate deployment of the implant 2 to the site of the lesion with ensured high quality.

Furthermore, the transition member 16 included in the implant delivery device according to this embodiment of the present invention can prevent the implant 2 from partially interfering with the sheath tube 13 seriously during the retrieval of the implant delivery device, which may cause damage to the implant 2.

Embodiment 2

The transition member 16 of Embodiment 1 is complicated in structure because it includes the transition section 161 and catheter section 162, in communication with each other. Such structural complexity will also complicate the implantation of the implant 2. In view of this, as shown in FIG. 5, an implant delivery device 1' according to Embodiment 2 includes a modified transition member 16.

As shown in FIG. 5, according to Embodiment 2, the transition member 16 includes only a transition section 161 without a catheter section 162. In this case, the transition section 161 is directly coupled, at a proximal end thereof, to the distal end of the bending controllable tube 17 by a smooth and fixed connection, and the axial movement of the transition section 161 is controlled by axial movement of the bending controllable tube 17. Other components of the implant delivery device 1' according to Embodiment 2 are the same as those of Embodiment 1, and a further description thereof is deemed unnecessary. Further, a method for implanting an implant by this implant delivery device 1' is the same as that of Embodiment 1, and a further description thereof is omitted here.

After the completion of the implantation of the implant 2, it is necessary to retrieve the catheter assembly in the implant delivery device 1'. First of all, the bending control mechanism of the bending controllable tube 17 is unlocked, and the handle 18 is manipulated to drive the bending controllable tube 17 to cause the transition section 161 move to distal end. As a result, the transition section 161 and the sheath tube 13 are at positions relative to each other, as shown in FIG. 5, where they are smoothly connected together. The catheter assembly is then retrieved from the patient's body by manipulating the handle 18.

In summary, in the implant delivery device according to embodiments of the present invention, the distal end of the sheath tube is fixed to the guide tip, and the implant is loaded at the proximal end of the sheath tube. During deployment of the implant, the sheath tube is caused to move to distal end, that is, the sheath tube continues moving toward the target site of the implant, rather than moves backward to the handle. This can effectively avoid the problems that may arise from retraction of the sheath tube through a three-dimensionally curved path, such as unstable or even faulty deployment of the implant. Moreover, in view of the fact that the implant is structured as having a radius greater in the inflow portion than in the outflow portion, it is designed that the inflow portion of the implant is released prior to the release of the outflow portion thereof. Once the inflow portion of the implant is deployed, a check against the target site may be performed, and the implant can be adjusted in a timely manner as soon as it is found that inaccurate positioning would take place. This enables more accurate deployment of the implant with enhanced quality. Further, the transition member arranged at the proximal end of the sheath tube can prevent the implant from partially interfering with the sheath tube seriously during the retrieval of the delivery device, which may cause damage to the implant.

The foregoing description is merely that of some preferred embodiments of the present invention and does not limit the scope thereof in any sense. Any and all changes in any form, such as equivalent substitutions or modifications, made by any person skilled in the art to the subject matter and teachings disclosed herein without departing from the scope of the present invention are considered to fall within the scope of the invention.

What is claimed is:

1. A delivery device for loading, delivering and deploying an implant, wherein the delivery device comprises a handle, an inner tubular core, a sheath tube, a guide tip, an inner tube, an anchor, a transition member, and a bending controllable tube, wherein the inner tubular core is coupled, at a proximal end thereof, to an inner tubular core actuation member arranged in the handle, wherein the guide tip is disposed at a distal end of the inner tubular core and fixedly connected to a distal end of the sheath tube, and wherein the sheath tube is configured to press and retain the implant, and is sleeved over the inner tubular core;

wherein the inner tube is disposed between the inner tubular core and the sheath tube, and the inner tube is fixed, at a proximal end thereof, to an inner tube fastener arranged in the handle;

wherein the anchor is in fixed connection with a distal end of the inner tube and is configured to retain the implant;

wherein the transition member is configured as a tubular structure sleeved over the inner tube; the transition member is disposed within the sheath tube; and the transition member and the sheath tube are partially fitted against each other;

wherein the transition member comprises a transition section and a catheter section in communication with the transition section, the transition section having a proximal end in smooth and fixed connection with a distal end of the catheter section, the catheter section being coupled, at a proximal end thereof, to a catheter actuation member arranged in the handle, wherein the transition section comprises a distal end smoothly and detachably coupled to the proximal end of the sheath tube;

wherein the transition section comprises a transition sidewall disposed between the proximal end and the distal end of the transition section, the transition sidewall having an outer diameter decreased from the distal end to the proximal end of the transition section, wherein a distal end of the bending controllable tube abuts against the transition sidewall and covers a portion of the transition sidewall along an axial direction of the bending controllable tube, and the bending controllable tube is not fixedly connected to the proximal end of the transition section; the bending controllable tube is coupled, at a proximal end thereof, to a bending controllable tube actuation member arranged in the handle; and the bending controllable tube comprises a bending control mechanism adapted to adjust an angle of deflection from the axial direction of the bending controllable tube;

wherein the bending controllable tube is embedded therein with at least one metal wire configured to be pulled to achieve a bending control of the bending controllable tube wherein the inner tube is limited by the handle at six degrees of freedom including three translational degrees of freedom along three orthogonal coordinate axes X, Y and Z and three rotational degrees of freedom about the axes X, Y and Z.

2. The delivery device of claim 1, wherein the guide tip has a conical shape, and wherein the distal end of the sheath tube is in smooth and fixed connection with a proximal end of the guide tip.

3. The delivery device of claim 1, wherein the sheath tube is smoothly and detachably coupled, at a proximal end thereof, to the transition member by static friction.

4. The delivery device of claim 1, wherein the bending controllable tube is sleeved over the catheter section.

5. The delivery device of claim 1, wherein the bending controllable tube is sleeved over the inner tube.

6. The delivery device of claim 1, wherein the transition sidewall of the transition section forms a half-cone structure, a hemisphere structure or a circular frustum structure.

7. The delivery device of claim 1, wherein the anchor has a plurality of grooves provided thereon.

8. The delivery device of claim 1, wherein the inner tubular core, the inner tube, the catheter section, the bending controllable tube and the sheath tube are arranged coaxially.

9. The delivery device of claim 1, wherein the inner tubular core passes through each of the inner tube, the bending controllable tube, the transition member and the sheath tube.

10. The delivery device of claim 1, wherein the implant is collapsible.

* * * * *